(12) United States Patent
Bray

(10) Patent No.: US 6,235,034 B1
(45) Date of Patent: May 22, 2001

(54) BONE PLATE AND BONE SCREW GUIDE MECHANISM

(76) Inventor: Robert S. Bray, 9911 W. Pico Blvd., Suite 200, Los Angeles, CA (US) 90035

( * ) Notice: Subject to any disclaimer, the term of this patent is extended or adjusted under 35 U.S.C. 154(b) by 0 days.

(21) Appl. No.: 09/177,885

(22) Filed: Oct. 23, 1998

Related U.S. Application Data

(60) Provisional application No. 60/063,035, filed on Oct. 24, 1997.

(51) Int. Cl.[7] ................................. A61B 17/56
(52) U.S. Cl. .................. 606/71; 606/61; 606/70
(58) Field of Search .................. 606/69, 70, 71, 606/61; 623/17

(56) References Cited

U.S. PATENT DOCUMENTS

| | | | |
|---|---|---|---|
| 3,426,364 | 2/1969 | Lumb | 3/1 |
| 3,695,259 | * 10/1972 | Yost | 606/69 |
| 4,599,086 | 7/1986 | Doty | 623/17 |
| 4,794,918 | 1/1989 | Wolter | 128/92 VP |
| 4,892,545 | 1/1990 | Day et al. | 623/17 |
| 4,904,261 | 2/1990 | Dove et al. | 623/17 |
| 4,917,704 | 4/1990 | Frey et al. | 623/17 |
| 4,955,908 | 9/1990 | Frey et al. | 623/17 |
| 5,123,926 | 6/1992 | Pisharodi | 623/17 |
| 5,397,364 | 3/1995 | Kozak et al. | 623/17 |
| 5,423,826 | 6/1995 | Coates et al. | 606/96 |
| 5,458,638 | 10/1995 | Kuslich et al. | 623/17 |
| 5,458,641 | 10/1995 | Jimenez | 623/17 |
| 5,522,899 | 6/1996 | Michelson | 623/17 |
| 5,534,027 | * 7/1996 | Hodorek | 606/69 |
| 5,951,558 | * 9/1999 | Fiz | 606/70 |

FOREIGN PATENT DOCUMENTS

0179695A1  4/1986  (EP).

OTHER PUBLICATIONS

Advertisement for Orion, "Anterior Cervical Plate System", Danek Medical, Inc., 1994.

* cited by examiner

Primary Examiner—Henry J. Recla
Assistant Examiner—Julian W. Woo
(74) Attorney, Agent, or Firm—Christie, Parker & Hale, LLP

(57) ABSTRACT

A bone plate comprises a base plate having at least two screw holes and at least two bone screws capable of securing the bone plate to a bone by insertion through the screw holes into the bone. The bone screws have heads shaped to toggle within the screw holes. A retaining plate is provided that is fixedly attachable to the base plate. The retaining plate covers at least a portion of each of the bone screws. The retaining plate and base plate each contain set screw apertures. A set screw is provided to retain the retaining plate in place over the base plate by screwing the set screw through the set screw apertures in the retaining plate and base plate. This design prevents the bone screw from backing out from the bone once screwed in through the base plate.

31 Claims, 10 Drawing Sheets

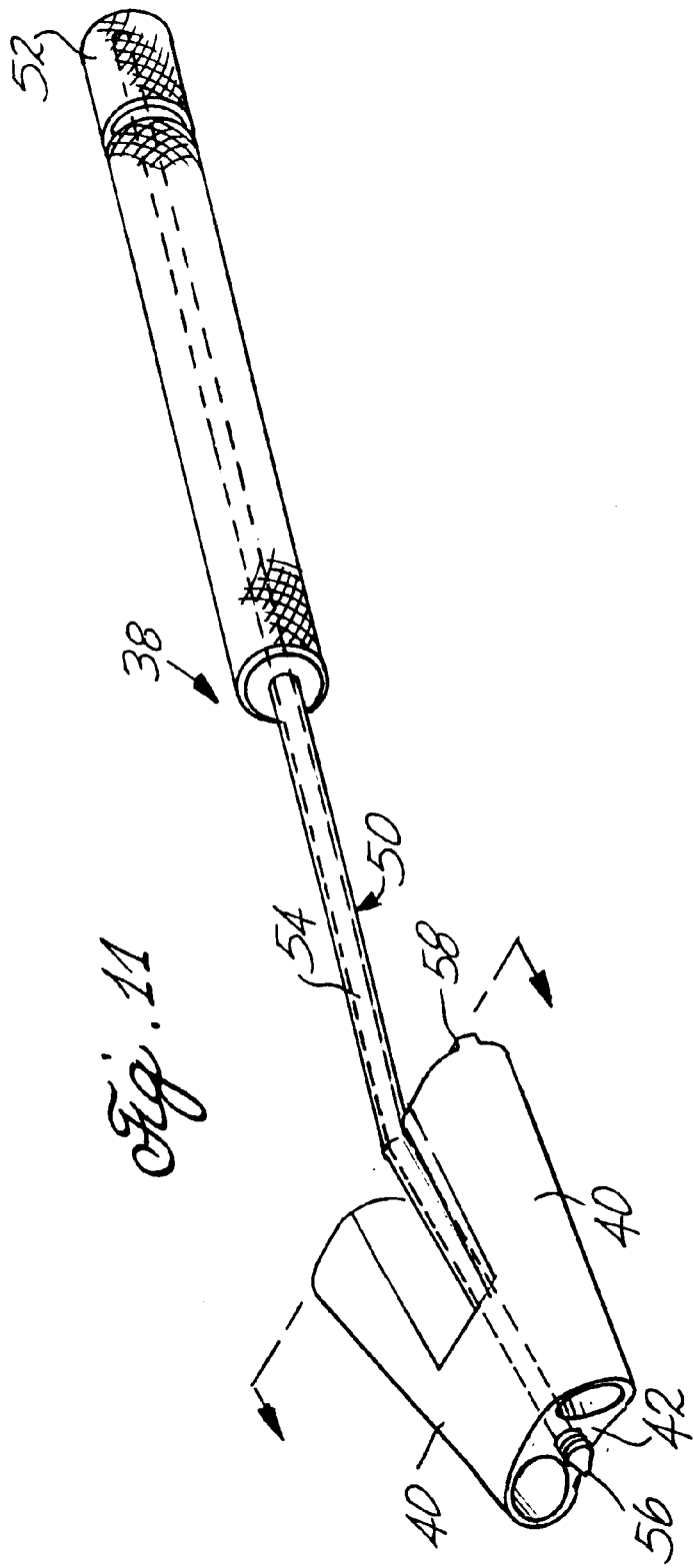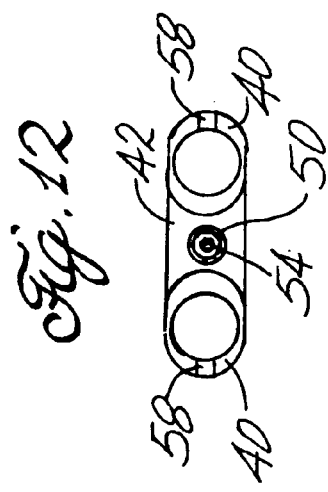

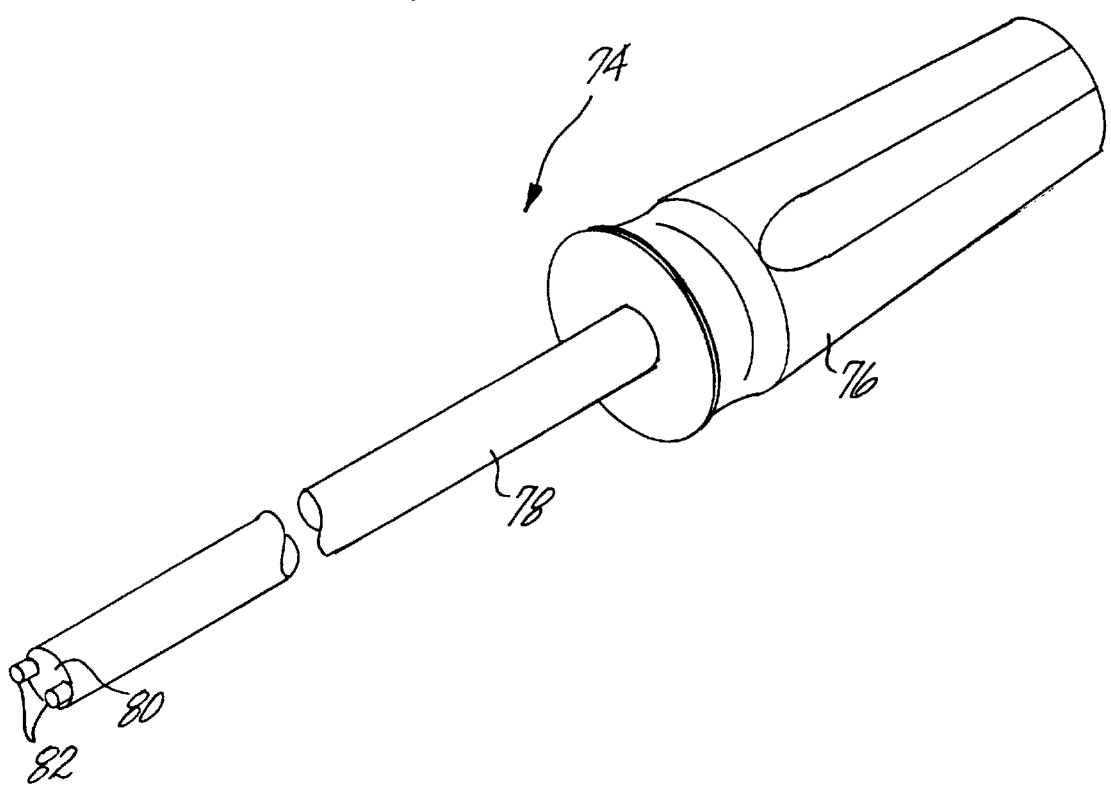

BONE PLATE AND BONE SCREW GUIDE MECHANISM

This application claims benefit of Provisional Application Ser. No. 60/063,035, filed Oct. 24, 1997.

FIELD OF THE INVENTION

The present invention is directed to a bone plate for assisting with the surgical arthrodesis (fusion) of two or more bones together, and a bone screw guide mechanism to assist in the proper drilling, tapping and placement of the bone screws to secure the plate.

BACKGROUND OF THE INVENTION

The spinal column of vertebrates provides support to bear weight and protection to the delicate spinal cord and spinal nerves. The spinal column comprises a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior which covers the neural structures. Between each vertebral body is an intervertebral disk, a cartilaginous cushion to help absorb impact and dampen compressive forces on the spine. To the posterior the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition congenital or acquired deformities can cause abnormal angulation or slippage of the spine. Slippage (spondylolisthesis) anterior of one vertebral body on another can cause compression of the spinal cord or nerves. Patients who suffer from one of more of these conditions often experience extreme and debilitating pain, and can sustain permanent neurologic damage if the conditions are not treated appropriately.

One technique of treating these disorders is known as surgical arthrodisis of the spine. This can be accomplished by removing the intervertebral disk and replacing it with bone and immobilizing the spine to allow the eventual fusion or growth of the bone across the disk space to connect the adjoining vertebral bodies together. The stabilization of the vertebra to allow fusion is often assisted by a surgically implanted device to hold the vertebral bodies in proper alignment and allow the bone to heal, much like placing a cast on a fractured bone. Such techniques have been effectively used to treat the above described conditions and in most cases are effective at reducing the patient's pain and preventing neurologic loss of function. However, there are disadvantages to the present stabilization devices and to the available tools to implant them.

The spinal fixation device needs to allow partial sharing of the weight of the vertebral bodies across the bone graft site. Bone will not heal if it is stress shielded from all weight bearing. The fixation device needs to allow for this weight sharing along with the micromotion that happens during weight sharing until the fusion is complete, often for a period of three to six months or longer, without breakage. The device must be strong enough to resist collapsing forces or abnormal angulation during the healing of the bone. Loss of alignment during the healing phase can cause a poor outcome for the patient. The device must be secure in its attachment to the spine to prevent migration of the implant or backout of the screws from the bone which could result in damage to the structures surrounding the spine, resulting in severe and potentially life threatening complications. The device must be safely and consistently implanted without damage to the patient.

Several types of anterior spinal fixation devises are in use currently. One technique involves placement of screws all the way through the vertebral body, called bicortical purchase. The screws are placed through a titanium plate but are not attached to the plate. This device is difficult to place, and overpenetration of the screws can result in damage to the spinal cord. The screws can back out of the plate into the surrounding tissues as they do not fix to the plate. Several newer generation devices have used a unicortical purchase of the bone, and in some fashion locking the screw to the plate to provide stability and secure the screw from backout. Problems have resulted from over ridged fixation and stress shielding, resulting in nonunion of the bony fusion, chronic micromotion during healing resulting in stress fracture of the fixation device at either the screw or the plate, insecure locking of the screw to the plate resulting in screw backout, or inadequate fixation strength and resultant collapse of the graft and angulation of the spine.

The conventional method for placing the bone screws entails drilling a hole, tapping the hole and threading the bone screw into the bone. To drill the hole a guide is held next to or attached to the plate. A drill is inserted into the guide and the hole drilled into the bone. The guide is removed and a tap is threaded through the hole attempting to follow the same angle as the drill hole. Caution must be used to prevent the sharp edges of the tap from damaging surrounding tissues or in creating too large a tap hole by toggling the handle of the tap. This will reduce the security of the screw bite into the bone and increases the likelihood of screw pullout. After tapping, the screw must be freehand guided at the proper angle into the hole created, inadvertent misalignment can reduce pullout strength or result in damage to surrounding nerves or arteries. Thus a need exists for a method of placing the screws that avoids these problems and risks to the patient.

SUMMARY OF THE INVENTION

The present invention is directed to a bone plate for stabilizing adjacent vertebrae or holding two portions of a bone together, e.g., a broken bone, while it heals. The bone plate comprises a base plate having at least two screw holes, at least two bone screws, and a bone screw locking means. The preferred bone screw locking means is a retaining plate. The bone plate is placed over at least two different bones or bone portions, and the bone screws are placed into each bone or bone portion through the bone screw holes in the base plate. The retaining plate is placed over the heads of the bone screws and fixedly attached to the base plate to prevent the bone screws from backing out of the bone. The bone screws have heads shaped to allow the bone screws to toggle within the screw holes in the base plate, preferably radiused heads. By controlling the amount of toggle, one can control the amount of weight borne by the bone plate.

The present bone plates are particularly useful for spinal fixation. For such a use, the base plate can be part of a larger device or structure. An example of such a device is a disk replacement spacer for stabilizing a portion of the spine. Such a device is described, for example, in U.S. patent application Ser. No. 08/764,089, the disclosure of which is incorporated herein by reference.

The present bone plates also can be used anywhere in the body where anti-backout is important, i.e., where it is important to be sure that bone screws will not back out. It also is particularly useful anywhere in the body where partial weight bearing of bone graft is important. Such uses include, for example, small figment bone sets from arm fractures, wrist fractures, ankle fractures, and hand fractures. The bone plate could also be used to secure hips in place, for femur fractures or the like.

The present invention is also directed to a bone screw guide mechanism for placing bone screws in the bones. The bone screw guide mechanism comprises a tubular member with open ends and a base fixedly attached at a predetermined angle to the tubular member at its bottom end. The base is mountable on the base plate of a bone plate so that the tubular member is generally coaxial with a bone screw hole in the base plate. Alternatively, the base can be mounted directly on the bone. Preferably, a handle is attached to the base or tubular member to provide ease of use. In a particularly preferred embodiment, an anchor screw is provided on the base of the bone screw guide mechanism to anchor the guide mechanism to the base plate during use.

The present invention is further directed to a method for inserting a bone screw into a bone through a base plate. A base plate having at least two bone screw holes is placed on a bone. The guide mechanism described above is placed on, and preferably mounted by means of a screw or the like, to the base plate so that the open bottom end of the tubular member is in communication the bone screw hole in the base plate. A drill is inserted through the tubular member and, through the bone screw hole, and a hole is drilled in the bone. Similarly, a tap is inserted through the tubular member to tap, i.e., create threads in the hole. A bone screw is then screwed into the drilled and tapped hole through the bone screw hole of the base plate. The guide mechanism can then be removed Use of the inventive bone screw guide mechanism assures that the user will drill and tap the hole at virtually the identical angle, thereby avoiding inadvertent widening of the hole as occurs in current procedures.

DESCRIPTION OF THE DRAWINGS

These and other features and advantages of the present invention will be better understood by reference to the following detailed description when considered in conjunction with the accompanying drawings wherein:

FIG. 11 is a perspective view of an embodiment of a bone screw guide mechanism according to the invention that has a handle.

FIG. 12 is a cross-sectional view of the bone screw guide mechanism of FIG. 11 across line 12—12.

FIG. 14 is a perspective view of a screwdriver for use in connection with the invention.

DETAILED DESCRIPTION

Figure 1:
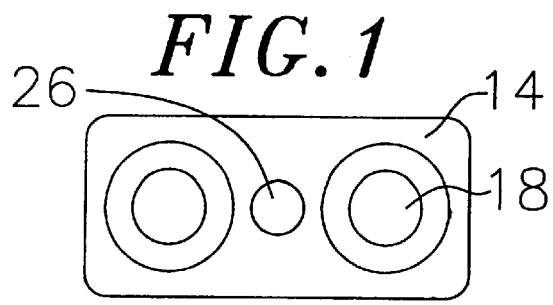
FIG. 1 is a frontal view of a base plate according to the invention.
Figure 2:
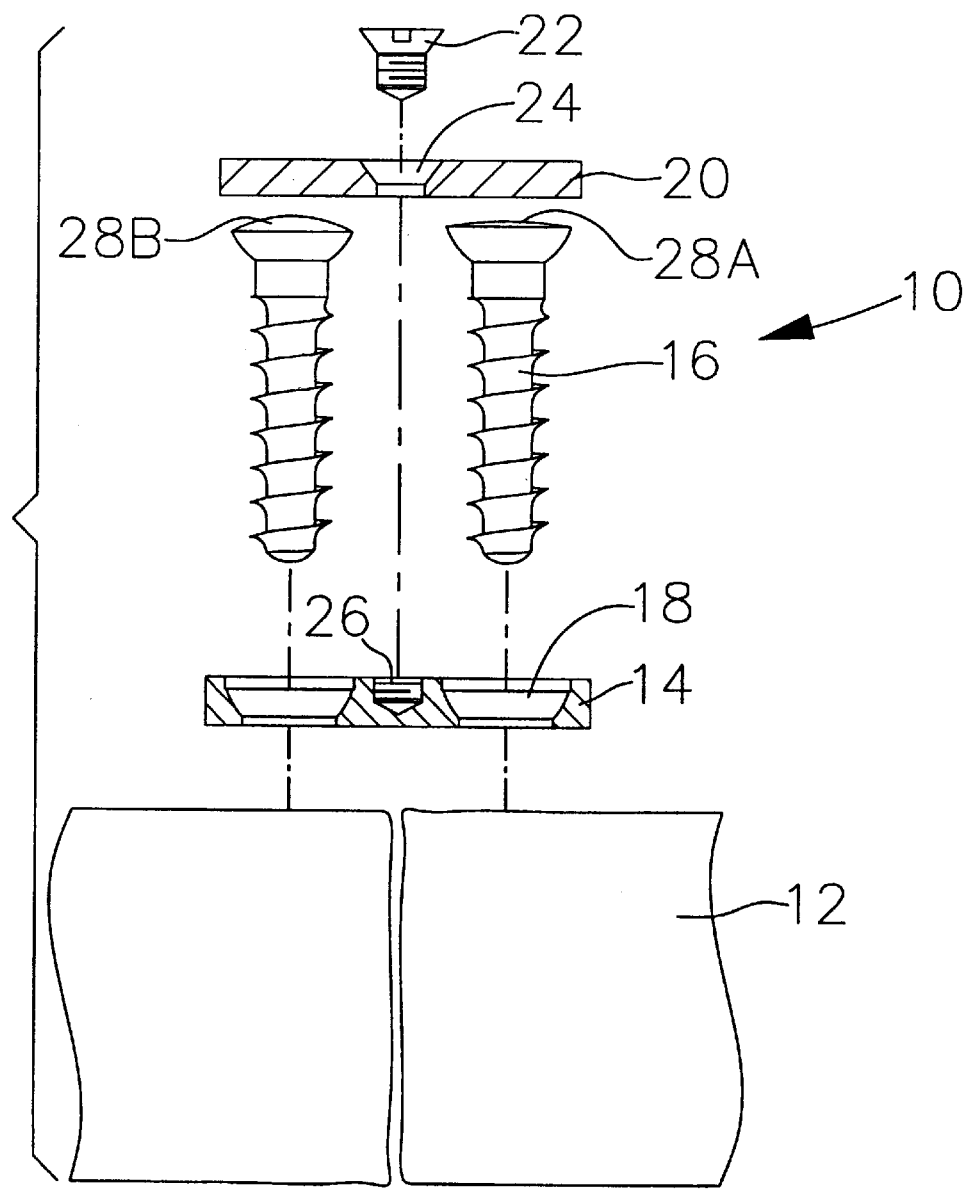
FIG. 2 is a side cross-sectional view of a bone screw locking mechanism according to the invention that is not assembled.
Figure 3:
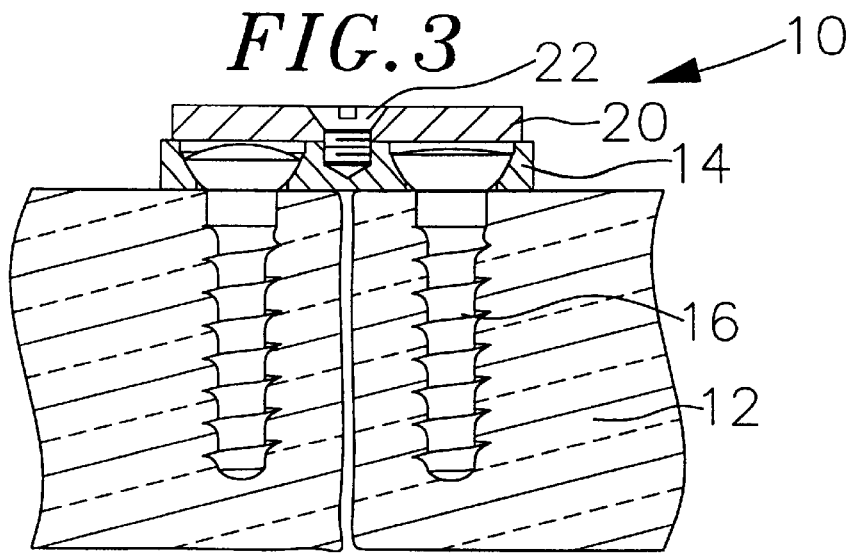
FIG. 3 is a side cross-sectional view of a bone screw locking mechanism according to the invention that is assembled.

A particularly preferred bone plate constructed in accordance with the present invention is shown in FIGS. 1 to 3. The bone plate 10 comprises a base plate 14, at least two bone screws 16, and at least one bone screw locking means.

The base plate 14 is a generally flat surface used to connect two or more bones 12. As used herein, the term "bones" is intended to include both bones and bone fragments or portions. The base plate 14 can be of any suitable shape or size. In the illustrated embodiment, the base plate 14 is a generally rectangular plate. The base plate 14 can be any other suitable shape, such as an oval, square, circle, triangle, or kidney shape or a combination thereof. As discussed above, the base plate 14 can also be part of a larger device. The embodiment depicted in FIGS. 1 to 3, however, is an independent base plate, i.e., is not part of a larger device.

The base plate 14 can be made of any suitable material, and is preferably made of titanium or a titanium alloy. The base plate 14 is generally flat, but can be slightly curved to fit against the particular bones 12 being connected. The thickness of the base plate 14 is not critical. When the base plate is made of titanium or titanium alloy, a thickness of from about 0.5 mm to about 3 mm, and more preferably from about 1 mm to about 2 mm is preferred.

The base plate 14 contains at least two bone screw holes 18 for receiving the bone screws 16. When the base plate 14 has only two bone screw holes 18, they are situated far enough apart so that the bone screws 16 received by the screw holes 18 can screw into different bones 12. In the illustrated embodiment, the base plate 14 also contains at least one set screw aperture 26 for receiving a set screw 22. Preferably the set screw aperture 26 is located near the center of the base plate 14.

Figure 4:
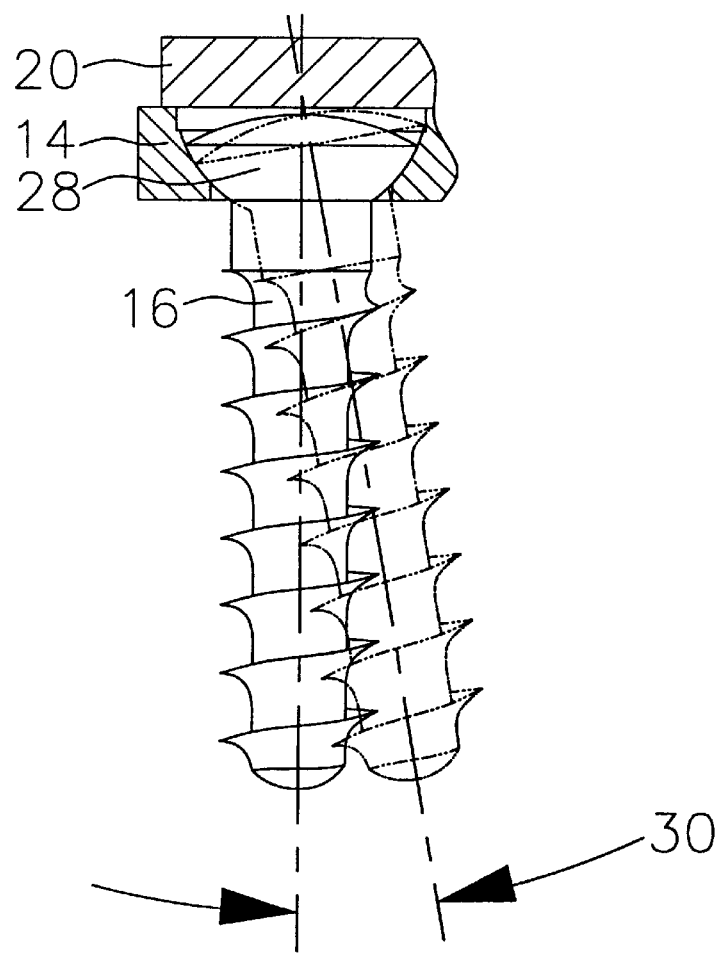
FIG. 4 is a side cross-sectional view of a bone screw according to the invention illustrating the degree of toggle of the screw.

The bone screws 16 can be made of any suitable material, and are preferably made of the same material as the base plate, which in the preferred embodiment is titanium or a titanium alloy. Each bone screws 16 has a head 28 that is capable of toggling within the screw hole 18, as depicted in FIG. 4. Preferably the bone screws 16 have a radiused head. As used herein, the term "radiused head" means that the lower portion of the bone screw head 28, i.e. the portion that is nearest the shank, is generally rounded. The bone screws 16 could have any other suitable shape that permits toggling, for example, where the portion nearest the shank is generally diagonal.

As shown in FIG. 2, the top portion of each bone screw head 28 can be flat 28a, slightly rounded 28b or even hemispherical. The more rounded the top of the bone screw head 28, the greater angle the bone screw 16 can toggle within the screw holes 18. By controlling the maximum angle that the bone screws 16 can toggle within the screw hole, one can control, at least in part, the amount of weight borne by the base plate 14.

Preferably the bone screw 16 can toggle within the screw hole 18 in at least two directions at an angle 30 of about 0 to about 20 or 30 degrees or more from normal depending on the circumstances. Still more preferably the bone screw 16 can toggle within the screw hole 18 in any direction at the above angles.

A bone screw locking means is any means for securedly covering at least one bone screw 16 so that the bone screw cannot back out from the bone 12 once screwed in through the base plate 14. A preferred bone screw locking means comprises a retaining plate 20 and a retaining plate fixing means.

The retaining plate 20 is a generally flat or slightly curved plate that lies preferably flush against the bone plate 14. The retaining plate 20 can be of any shape or size such that it covers at least a part of at least one bone screw 16. More preferably the retaining plate 20 covers at least part of each bone screw 16 in an associated pair of bone screws 16. However, multiple retaining plates 20 can be used to cover different bone screws 16.

In the illustrated embodiment, the retaining plate 20 is a generally flat rectangular plate, similar to the base plate 14. The retaining plate covers each bone screw 16 of an associated pair of bone screws. Preferably the retaining plate 20 covers 100 percent of the bone screw 16 or screws, but may cover less. Thus, when the retaining plate 20 is secured to the base plate 14, the bone screws 16 cannot back out from the base plate 14. The thickness of the retaining plate 20 preferably ranges from about 0.5 mm to about 2 mm, and more preferably from about 1 mm to about 1.5 mm.

The retaining plate 20 can be fixedly attached to the base plate 14 by any suitable retaining plate fixing means. In a preferred embodiment, the retaining plate 20 is attached to the base plate 14 with one or more set screws 22. The set screw 22 is placed through a set screw hole 24 in the retaining plate 20, inserted through the set screw aperture 26 in the base plate 14, and tightened to secure the retaining plate 20 to the base plate 14. The set screw can be made of any suitable material well known in the art, preferably titanium or a titanium alloy. In the preferred embodiment, the set screw is an hexagonal set screw that can be turned with an hexagonal driver. Other types of set screws can also be used.

Figure 5:
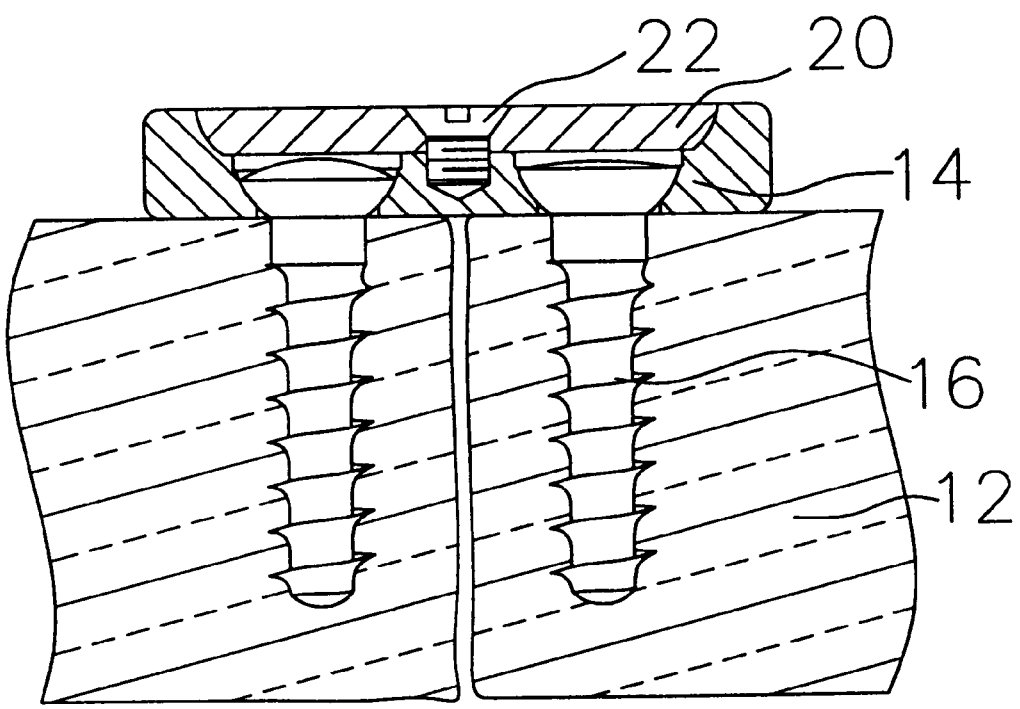
FIG. 5 is a side cross-sectional view of an alternative bone screw locking mechanism according to the invention where the retaining plate is situated in a recess in the base plate created by a raised structure on all four sides of the screw holes.
Figure 6A:
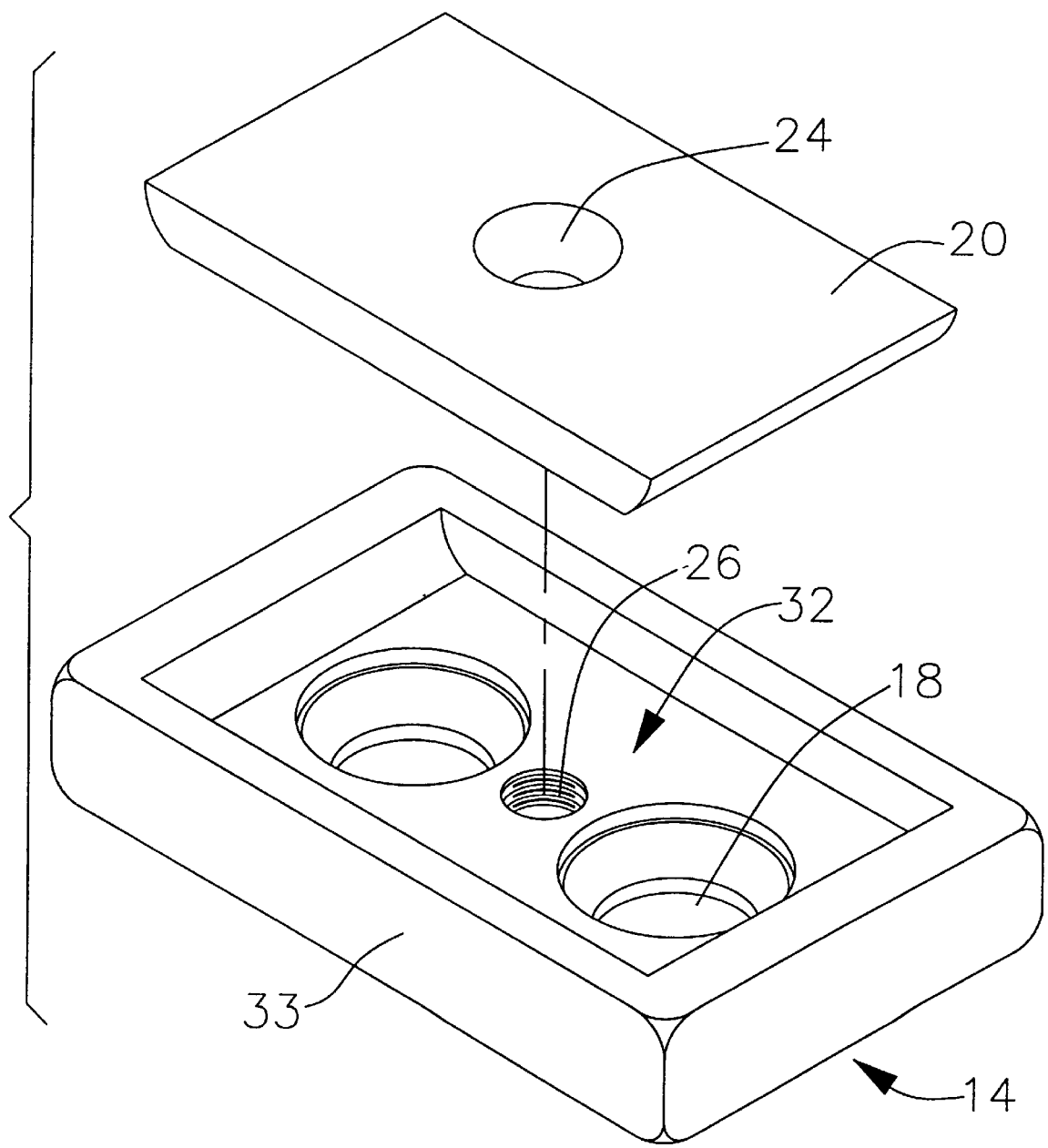
FIG. 6a is a projectional view of the bone plate of the embodiment of FIG. 5.
Figure 6B:
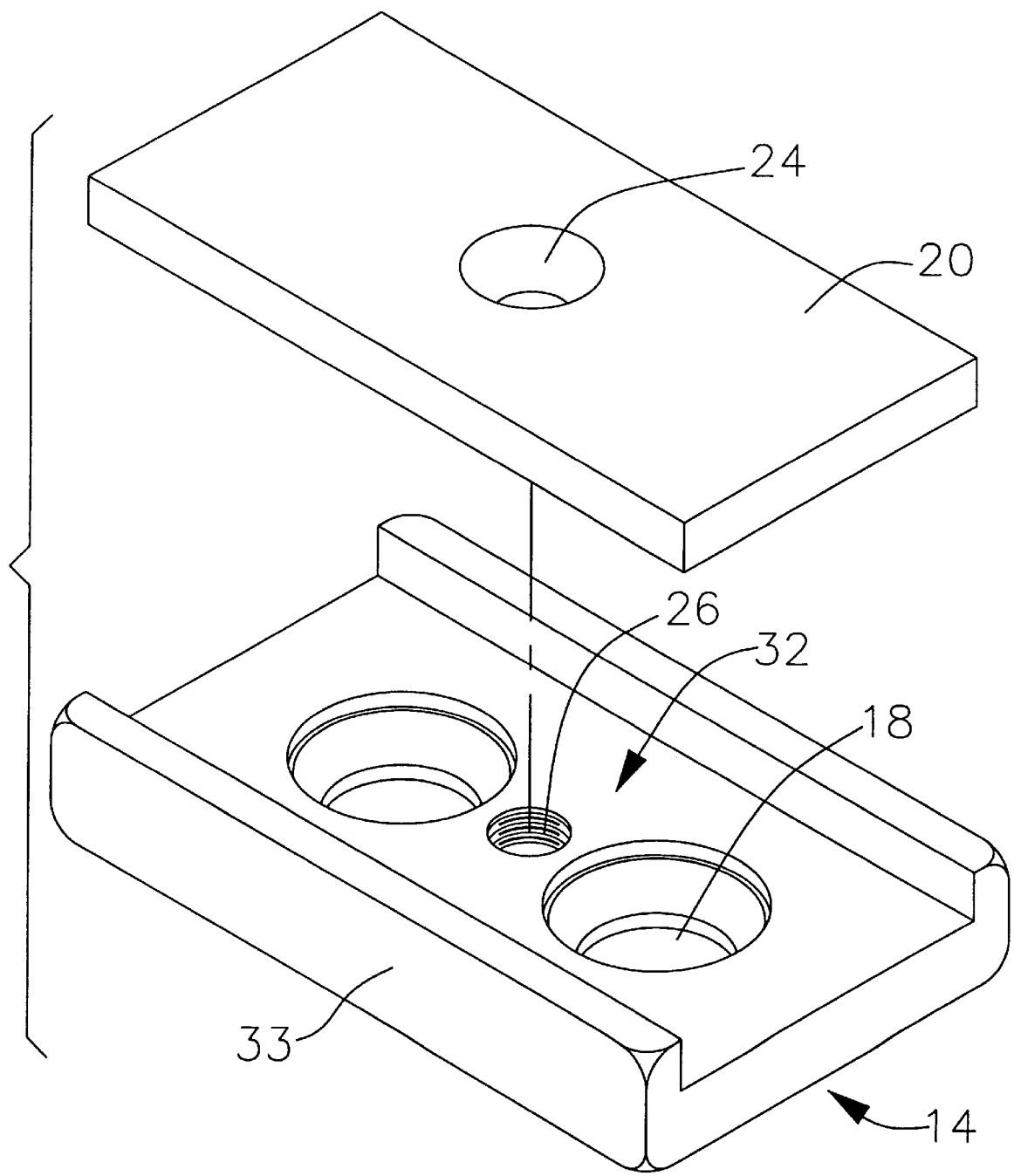
FIG. 6b is a projectional view of an alternative embodiment of the bone plate of FIG. 6a where the recess in the base plate is created by raised structures on only two sides of the screw holes.

An alternative embodiment of a bone plate according to the present invention is illustrated in FIGS. 5, 6a and 6b. The bone plate 14 comprises a recess 32 for receiving the retaining plate 20. The recess 32 can be any shape or size. Preferably the recess 32 and retaining plate 20 are of a similar shape and size such that the retaining plate 20 fits snugly within the recess 32. The recess 32 is defined by a raised structure 33 that forms a boundary around at least a portion of the retaining plate area. FIG. 6a depicts a recess 32 where the raised structure 33 surrounds all four sides of the retaining plate area. FIG. 6b depicts an alternative embodiment of a recess 32 where the raised structure 33 is situated on only two sides of the retaining plate area. Alternatively, the raised structure 33 can be situated on only one side of the retaining plate area, as shown, for example, in FIG. 7, discussed in more detail below.

Figure 7:
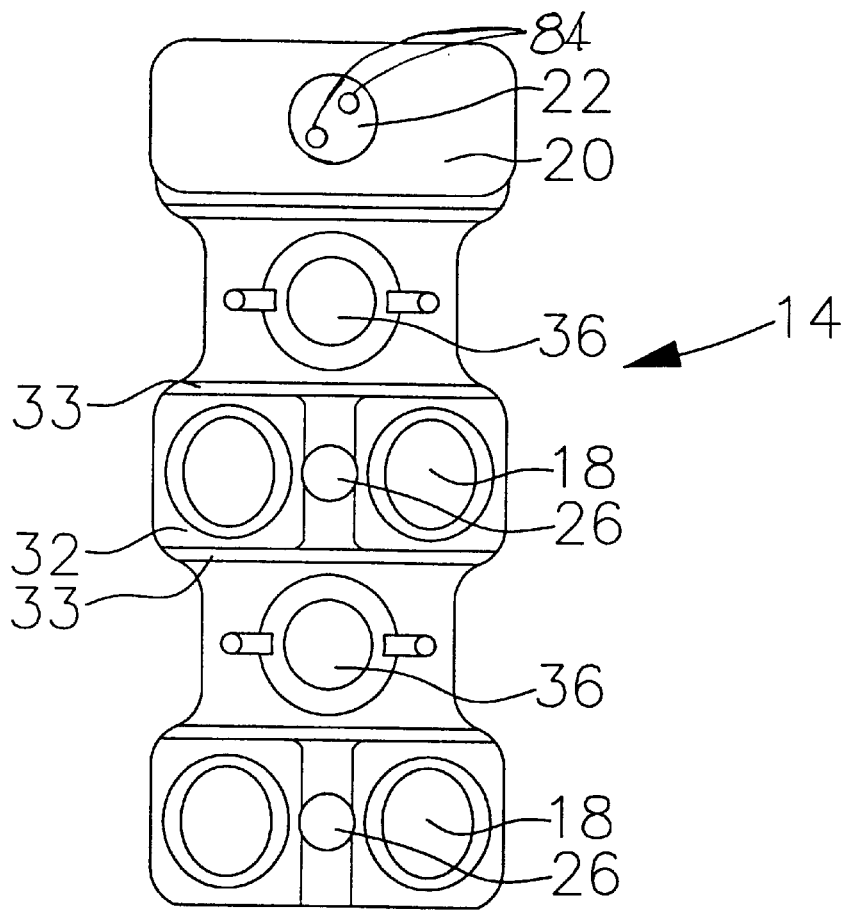
FIG. 7 is a frontal view of another alternative bone screw locking mechanism according to the invention where the bone plate has six bone screw holes.

The alternative embodiment depicted in FIG. 7 is particularly useful for fixation of three adjacent vertebrae. This design can be used in combination with a disk replacement spacer, such as that described in U.S. patent application Ser. No. 08/764,089. In the embodiment shown, the base plate 14 contains three pairs of associated screw holes 18. With this design, two bone screws 16 are screwed into each vertebra 12. Between each adjacent screw holes 18 of a pair of screw holes is a set screw hole 26. A separate retaining plate 20 covers each pair of adjacent screw holes 18. In FIG. 7, the top pair of adjacent screw holes 18 is shown covered with a retaining plate 20. In this embodiment, the base plate has raised ribs which extend adjacent 33 the long sides of each retaining plate 20. The ribs 33 create a recess 32 for receiving the retaining plate 20. This embodiment also contains spacer screw holes 36 for receiving spacer screws (not shown). The spacer screws allow the base plate 14 to be secured to a disk replacement spacer, such as that described in U.S. patent application Ser. No. 08/764,089. The spacer screw holes 36 are situated between the pairs of adjacent screw holes 18.

Figure 8:
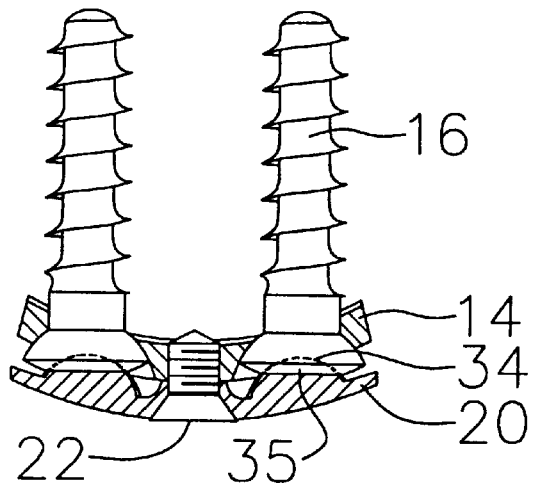
FIG. 8 is a side cross-sectional view of another embodiment of a bone screw locking mechanism according to the invention showing an alternative design for the bone screws and retaining plate.

FIG. 8 shows an additional embodiment of a bone plate having an alternative design for the bone screws 16 and retaining plate 20. Each bone screw head 28 contains a depression 34, preferably a rounded depression. At the nadir of the depression 34 is an hexagonal socket or the like so that the screw can be turned by an hexagonally shaped driver, e.g., an Allen wrench. The retaining plate 20 contains protrusions 35, preferably hemispherically-shaped protrusions, preferably with radially extending ribs that correspond generally in shape, size and number to depressions 34 and fit within the depressions 34 in the bone screw heads 28. As in the embodiments described above, the bone screw head 28 is a radiused head such that the bone screw 16 can toggle within the screw hole 18.

Figure 9:
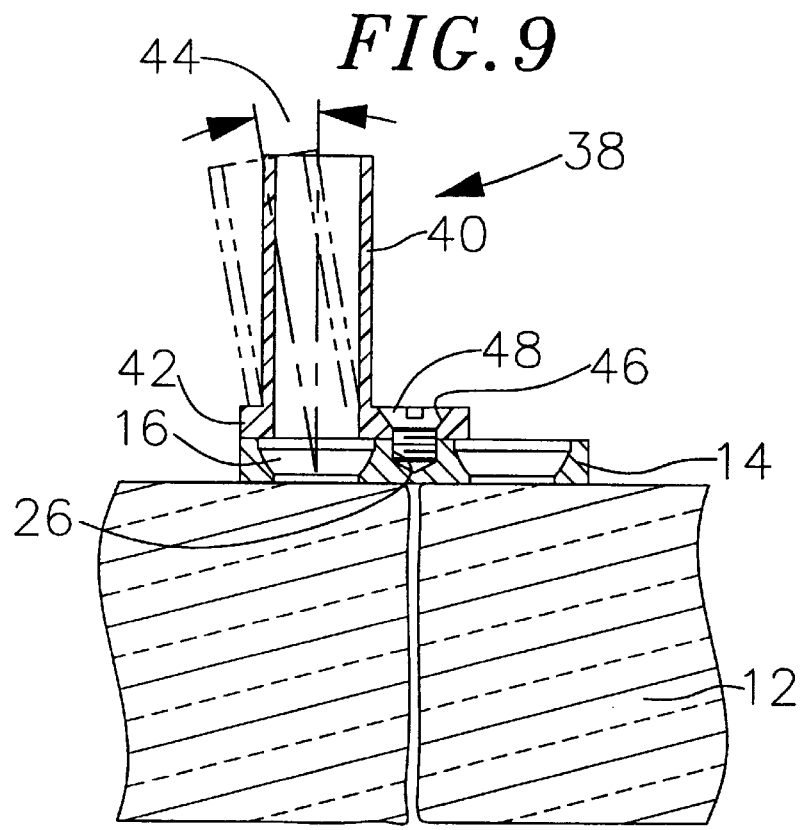
FIG. 9 is a cross-sectional view of an embodiment of a bone screw guide mechanism of the invention having a single tubular member.

Another aspect of the present invention is a bone screw guide mechanism 38 for putting in the bone screws 16. As shown in FIG. 9, the guide mechanism 38 comprises a generally tubular member 40 fixedly attached to a base 42. The top and bottom ends of the tubular member 40 are open.

The tubular member 40 is at a predetermined angle 44 to the base 42 which is the same angle as the desired angle of the screw holes in the bone. In practice, the base 42 of the guide mechanism 38 is placed flush on a base plate 14 such that the open end of the tubular member 40 is in communication with the bone screw hole 16 in the base plate 14.

The user can insert a drill through the tubular member 40 to drill a hole in the bone 12 through the bone screw hole 16. The user can then tap the hole in the bone without removing the guide mechanism 38 by inserting a tapping tool through the tubular member 40. Once the hole is drilled and tapped, the guide mechanism 38 is removed and a bone screw 16 is inserted into the screw hole 18 in the base plate 14.

The angle of the tubular member is selected based on the particular application. Preferably the tubular member 40 forms an angle 44 with the base 42 ranging from about 0 to about 20 or 30 degrees or more from normal, more preferably from about 0 to about 15 degrees from normal. The tubular member 40 can be made of any suitable material and is preferably made of titanium or stainless steel. The length and inner diameter of the tubular member will vary according to the application and the size of the bone screws involved. Tubular members 40 typically have an inner diameter ranging from about 2 mm to about 7 mm. The thickness of the tubular member is not critical.

The base 42 can be of any suitable shape, but is preferably generally rectangular. The base 42 may be generally flat or have any other cross-sectional shape that permits it to lie preferably flush against the base plate 14. Like the tubular member, the thickness of the base is not critical. Thicknesses of about 1 mm to about 4 mm are preferred.

The tubular member 90 and base 42 are preferably a one piece unitary construction. However, two piece constructions in which the tubular member 40 is fixedly attachable or even removably attachable to the base may be used.

Multiple guide mechanisms 38 where the tubular members 40 form different angles with the base 42 can be packaged in the form of a kit.

In a preferred embodiment, as shown in FIG. 9, the base 42 contains a screw hole 46 for receiving a lock screw 48. The lock screw 48 can be used to fixedly attach the base 42 to a base plate 14. The lock screw 48 is inserted through the screw hole 46 in the base 42 and through the set screw aperture 26 in the base plate 14.

Figure 10:
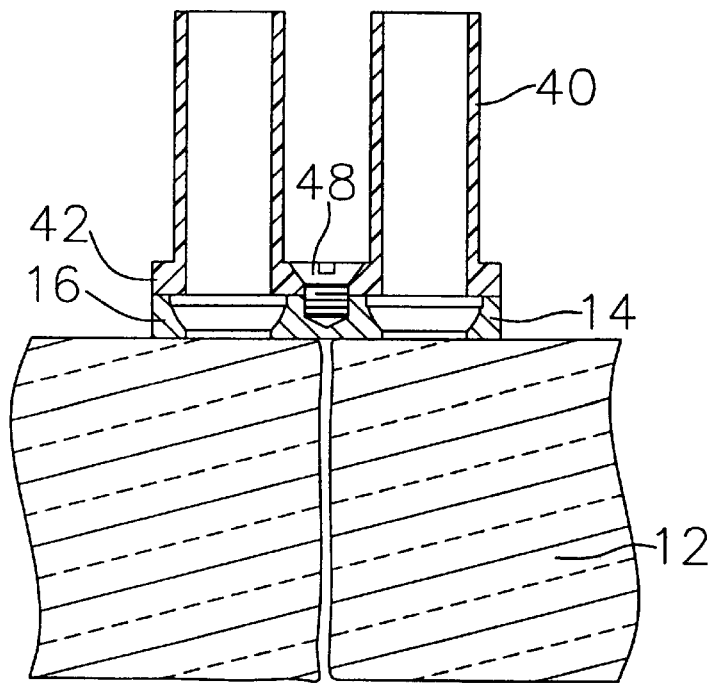
FIG. 10 is a cross-sectional view of an alternative embodiment of a bone screw guide mechanism of the invention having multiple tubular members.

In the embodiment shown in FIG. 9, the guide mechanism 38 comprises a single tubular member. An alternative embodiment is shown in FIG. 10. In this embodiment, the guide mechanism 38 comprises two elongated tubular members 40 fixedly attached to a single base 42. The base has a rectangular shape, but can have any shape similar to the base plate 14 with which it is to be used so that it can sit flush against the base plate. This base 42 design is particularly suitable for use with a base plate 14 as shown in FIG. 7, where each pair of adjacent bone screw holes 18 has two raised structures 33 on the longer sides of the rectangular section of the base plate 14 in which they are located. The base 42 can thus be placed into the recess 32 formed by the two raised structures 33.

Any means for fixedly attaching or situating the base 42 on the base plate 14 can be used and are considered to be within the scope of the invention. If desired, the guide mechanism 38 may be designed to be mounted on the base plate 14 and held in place manually during drilling and tapping.

Another alternative embodiment of a bone screw guide mechanism 38 is depicted in FIGS. 11 and 12. Similar to the embodiments described above, the guide mechanism 38 comprises two generally tubular members 40 both fixedly attached to a base 42. The top and bottom ends of each tubular member 40 are open. A handle 50 having proximal and distal end is anchored at its distal end to or near the base 42. The handle 50 extends proximally away from the tubular members 40. The proximal end of the handle 50 comprises a turnable knob 52. The knob 52 is attached to a cable 54 having proximal and distal ends that extends within the handle 50. The distal end of the cable 54 is attached to a threaded anchoring screw 56 that extends distally from the base 42. Turning the knob 52 turns the cable 54, which, in turn, turns the anchoring screw 56.

In preferred practice, a base plate 14 is placed directly on the bone into which the screws are to be inserted, and the guide mechanism 38 is placed over the base plate 14. The anchoring screw 56 is used to hold the bone screw guide mechanism 38 in place against the base plate 14 by screwing the anchoring screw 56 into set screw aperture 26 of the base plate 14 until the face of the base 42 of the guide mechanism 38 is flush against the base plate 14. A drilling tool having an elongated stem is inserted through each tubular member 40 to drill holes in the bone. If desired before drilling, a tack tool, a tool having an elongated stem and a removable sharp tack at its distal end, may be inserted through each tubular member and pushed distally so that the tack creates a starter hole in the bone to facilitate drilling. After drilling, a tapping tool is inserted through each tubular member to tap the drilled holes. The stems of the tack tool, drilling tool and tapping tool have generally the same diameter which is slightly less than the inner diameter of the tubular members 40 of the guide mechanism of such that the stems of the tools may be slidably received in the tubular members but are afforded no or almost no lateral "play." Following tapping, bone screws 16 are screwed into the drilled and tapped holes through the bone screw holes 18 in the base plate 14.

The angle of the face of base 42 of the guide mechanism 38 determines the angle at which the bone screws 16 will be secured in the bone. For example, when the face of the guide mechanism base 42 is normal, i.e., 90° to the axis of the tubular members 40, the holes drilled and tapped into the bone will be normal to the base plate 14 and to the face of the bone. Such a guide mechanism is referred to herein as an 0° guide. If the face of the base 42 of the guide mechanism 38 is at a selected angle other than 90° from the axis of the tubular members 40, then the holes drilled and tapped into the bone will be at an angle other than normal to the base plate and face of the bone. A guide mechanism 38 which provides for the drilling and tapping of holes at an angle 15° above that created by an 0° guide is referred to herein as a 15° guide and so on.

Figure 13:
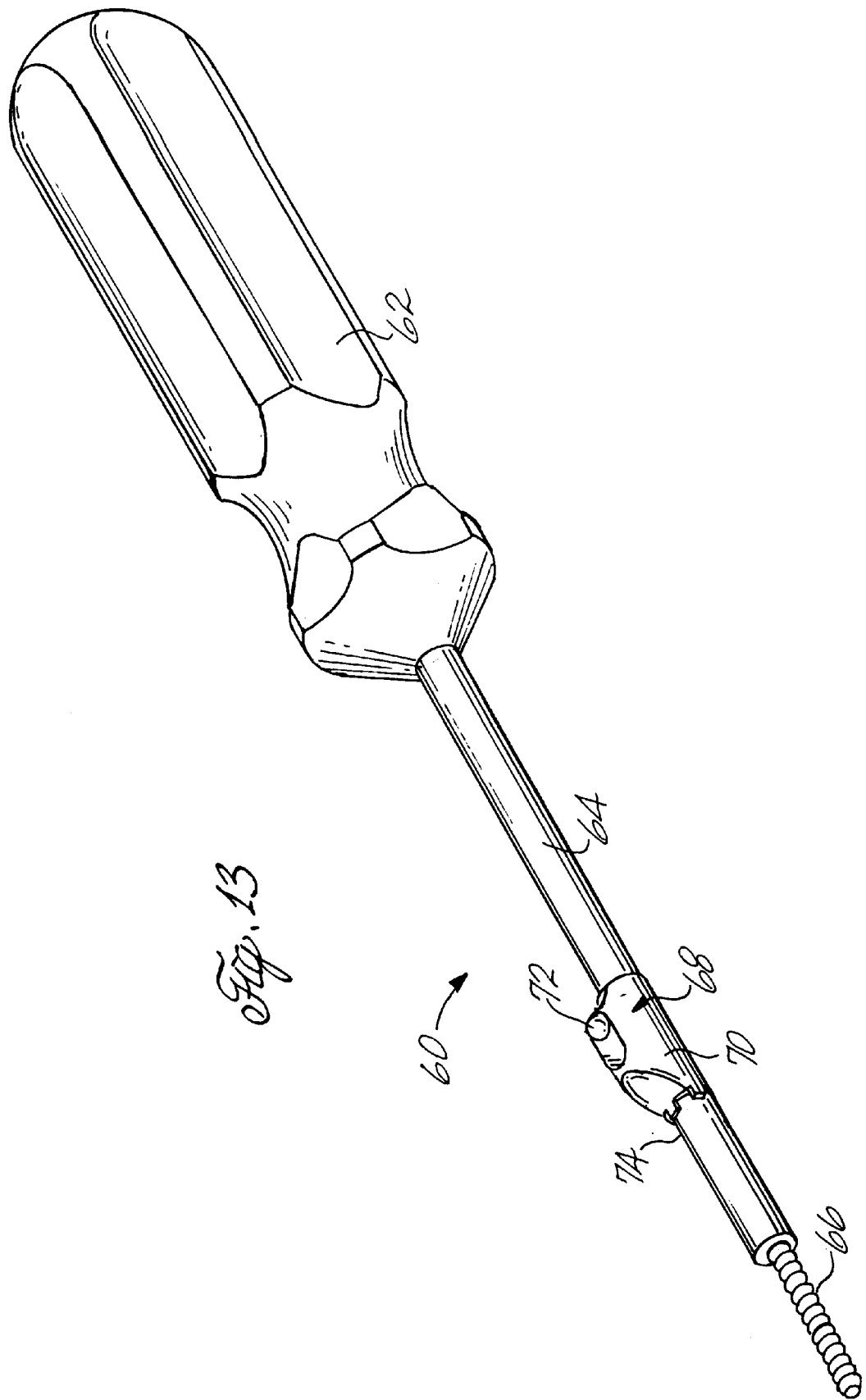
FIG. 13 is a perspective view of a tapping tool for use in connection with the invention.

The proximal end of each tubular member 40 of the guide mechanism 38 comprises a protrusion 58. This feature is beneficial when the bone screw guide mechanism 38 is used with the tapping tool 60 depicted in FIG. 13. The tapping tool 60 comprises a handle 62, a stem 64, and a threaded tap 66. Mounted on the stem 64 is an adjustable depth guide 68. The depth guide 68 comprises a slidable housing 70 and a spring loaded pin 72. When pressure is exerted on the pin 72, the slidable housing 70 can be slid between two or more positions along the length of the stem 64. The position of the depth guide 68 on the stem 64 dictates the depth that the tap 66 and stem 64 can be inserted into the tubular member 40 of the guide mechanism 38. The housing 70 comprises protrusions 72 at its distal end. As the tapping tool 60 is rotated within the tubular member 40 of the guide mechanism 38 and reaches the depth dictated by the depth guide 68, one of the protrusions 72 on the depth guide housing will engage protrusion 58 on the tubular member 40 of the guide mechanism, preventing further rotation of the tapping tool 60. This mechanism prevents stripping of the tapped hole in the bone that would result from further rotation of the tapping tool 60.

The depth guide 38 described above is also useful for the drilling tool. However, for a drilling tool, it is unnecessary to include protrusions on the depth guide housing.

An additional tool useful in connection with the present invention, a screwdriver, is depicted in FIG. 14. The screwdriver 74 comprises a handle 76, a stem 78, and a head 80. The head 80 comprises two rounded protrusions 82, generally on opposite sides of the head. The protrusions 82 fit into corresponding holes 84 provided in the head of a screw, for example, as shown in FIG. 7. It is understood that the number and shape of the protrusion, 82 may vary as desired.

For example, a single axial hexagonal protrusion may be used in conjunction with screws having a corresponding axial hexagonal hole in the screw head.

Further, it is understood that, if desired, the guide mechanism of the type described above may comprise only a single tubular member along with a handle. Means may or may not be provided for anchoring the guide mechanism to a base plate 14. Consequently, a guide mechanism used entirely free hand is contemplated by and within the scope of this invention.

It is presently preferred to provide a kit having base plates of differing sizes, bone screws of differing lengths and locking plates complementary to the base plates. The kit may further comprise one or more guide mechanisms, preferably at least an 0° guide and a 15° guide, a tack tool, a drilling tool, tapping tool and/or one or more screw driving tools.

While embodiments and applications of this invention have been shown and described it would be apparent to those skilled in the art that many more modifications are possible without departing from the inventive concepts herein. The invention, therefore, is not to be restricted except in the spirit of the appended claims.

What is claimed is:

1. A bone plate comprising:
   a base plate having at least two screw holes;
   at least two bone screws capable of securing the bone plate to a bone by insertion through the screw holes into the bone, wherein the bone screws have heads shaped to toggle within the screw holes; and
   a bone screw locking means capable of securedly covering the bone screws so that the bone screws cannot back out from the bone once screwed in through the base plate;
   wherein the bone screws and bone screw locking means are designed such that when the bone screw locking means covers the bone screws and is fixedly attached to said base plate, the top of each bone screw mates with the bone screw locking means and each bone screw can toggle within its corresponding screw hole.

2. A bone plate according to claim 1, wherein the bone screw locking means comprises:
   a retaining plate fixedly attachable to the base plate, wherein the retaining plate covers at least a portion of each of the bone screws, and
   a retaining plate fixing means for fixedly attaching the retaining plate to the base plate.

3. A bone plate according to claim 2, wherein the fixing means comprises a set screw and wherein the base plate also has a set screw aperture.

4. A bone plate according to claim 2, wherein the retaining plate covers 100 percent of at least one bone screw.

5. A bone plate according to claim 1, wherein each bone screw can toggle within the corresponding screw hole in at least two directions at an angle of about 0 to about 20 degrees from normal.

6. A bone plate according to claim 1, wherein each bone screw can toggle within the corresponding screw hole in at least two directions at an angle of about 0 to about 15 degrees from normal.

7. A bone plate according to claim 1, wherein each bone screw can toggle within the corresponding screw hole in any direction at an angle of about 0 degrees to about 20 degrees from normal.

8. A bone plate according to claim 1, wherein each bone screw can toggle within the corresponding screw hole in any direction at an angle of about 0 to about 15 degrees from normal.

9. A bone plate according to claim 1, wherein each bone screw has a radiused head.

10. A bone plate according to claim 2, wherein each bone screw head contains a depression and wherein the retaining plate contains protrusions that correspond in shape, size and number to and that are capable of fitting within the depressions in the bone screw heads.

11. A bone plate according to claim 10, wherein each bone screw has a radiused head.

12. A bone plate according to claim 1, wherein the base plate comprises at least two pairs of adjacent screw holes.

13. A bone plate according to claim 1, wherein the base plate is made of titanium or a titanium alloy.

14. A bone plate comprising
   a base plate having two screw holes and a set screw hole between the screw holes;
   two bone screws capable of securing the bone plate to a bone by insertion through the screw holes into the bone;
   a retaining plate fixedly attachable to the base plate, wherein the retaining plate has a size sufficient to cover the bone screws and a set screw aperture extending therethrough so that the set screw aperture is aligned with the set screw hole in the base plate when the retaining plate is placed on the base plate; and
   a set screw for fixedly attaching the retaining plate to the base plate by extending through the set screw aperture in the retaining plate and into the set screw hole in the base plate;
   wherein the bone screws and retaining plate are designed such that, when the retaining plate covers the bone screws the top of each bone screw mates with the retaining plate and the covered bone screws can toggle within the screw holes.

15. A bone plate according to claim 14, wherein each bone screw has a radiused head.

16. A bone plate according to claim 14, wherein each bone screw head contains a depression and wherein the retaining plate contains protrusions that correspond in shape, size and number to and that are capable of fitting within the depressions in the bone screw heads.

17. A bone plate according to claim 16, wherein each bone screw has a radiused head.

18. A bone plate according to claim 14, wherein each bone screw can toggle within the corresponding screw hole in at least two directions at an angle of about 0 to about 20 degrees from normal.

19. A bone plate according to claim 14, wherein each bone screw can toggle within the corresponding screw hole in at least two directions at an angle of about 0 to about 15 degrees from normal.

20. A bone plate according to claim 14, wherein each bone screw can toggle within the corresponding screw hole in any direction at an angle of about 0 to about 20 degrees from normal.

21. A bone plate according to claim 14, wherein each bone screw can toggle within the corresponding screw hole in any direction at an angle of about 0 to about 15 degrees from normal.

22. A bone plate according to claim 14, wherein the base plate and retaining plate are both made of titanium or a titanium alloy.

23. A bone plate comprising
   a base plate having two screw holes, a set screw hole between the screw holes and at least two raised edges;
   two bone screws capable of securing the base plate to a bone by insertion through the screw holes into the bone wherein each bone screw is adapted to toggle within each screw hole;

a retaining plate fixedly attachable to the base plate, wherein the retaining plate has a size sufficient to cover the bone screws and fit within the at least two raised edges, and wherein the retaining plate includes a set screw aperture extending therethrough so that the set screw aperture is aligned with the set screw hole in the base plate when the retaining plate is placed on the base plate; and a set screw for fixedly attaching the retaining plate to the base plate by extending through the set screw aperture in the retaining plate and into the set screw hole in the base plate.

24. A bone plate according to claim 23, wherein the bone screws have heads shaped to toggle within the screw holes, and wherein, in use, the bone screw locking means covers the at least one bone screw, and the at least one covered bone screw can toggle within its corresponding screw hole.

25. A bone plate according to claim 23, wherein each bone screw has a radiused head.

26. A bone plate according to claim 23, wherein each bone screw head contains a depression and wherein the retaining plate contains protrusions that correspond in shape, size and number to and that are capable of fitting within the depressions in the bone screw heads.

27. A bone plate according to claim 26, wherein each bone screw has a radiused head.

28. A bone plate according to claim 23, wherein each bone screw can toggle within the corresponding screw hole in at least two directions at an angle of about 0 to about 20 degrees from normal.

29. A bone plate according to claim 23, wherein each bone screw can toggle within the corresponding screw hole in at least two directions at an angle of about 0 to about 15 degrees from normal.

30. A bone plate according to claim 23, wherein each bone screw can toggle within the corresponding screw hole in any direction at an angle of about 0 to about 20 degrees from normal.

31. A bone plate according to claim 23, wherein each bone screw can toggle within the corresponding screw hole in any direction at an angle of about 0 to about 15 degrees from normal.

* * * * *